(12) United States Patent
Kikugawa et al.

(10) Patent No.: US 8,609,591 B2
(45) Date of Patent: Dec. 17, 2013

(54) HERBICIDAL COMPOSITION

(75) Inventors: Hiroshi Kikugawa, Osaka (JP); Yoshikazu Satake, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 0 days.

(21) Appl. No.: 13/880,599

(22) PCT Filed: Oct. 18, 2011

(86) PCT No.: PCT/JP2011/074373
§ 371 (c)(1), (2), (4) Date: Apr. 19, 2013

(87) PCT Pub. No.: WO2012/053652
PCT Pub. Date: Apr. 26, 2012

(65) Prior Publication Data
US 2013/0210628 A1    Aug. 15, 2013

(30) Foreign Application Priority Data

Oct. 22, 2010  (JP) ................................. 2010-237558

(51) Int. Cl.
A01N 43/36    (2006.01)
A01N 43/00    (2006.01)

(52) U.S. Cl.
USPC ......................................... 504/138; 504/139

(58) Field of Classification Search
None
See application file for complete search history.

(56) References Cited

U.S. PATENT DOCUMENTS

| | | | |
|---|---|---|---|
| 5,968,873 A | 10/1999 | Dahmen et al. | |
| 5,998,334 A | 12/1999 | Murai et al. | |
| 6,821,926 B1 | 11/2004 | Feucht et al. | |
| 8,030,498 B2 | 10/2011 | Shimoharada et al. | |
| 8,119,569 B2 | 2/2012 | Komyoji et al. | |
| 8,435,928 B2 | 5/2013 | Kikugawa et al. | |
| 8,466,088 B2 | 6/2013 | Shimoharada et al. | |
| 8,466,089 B2 | 6/2013 | Tsukamoto et al. | |
| 2010/0317528 A1 | 12/2010 | Shimoharada et al. | |
| 2011/0190126 A1 | 8/2011 | Hall et al. | |
| 2011/0263427 A1 | 10/2011 | Kikugawa et al. | |
| 2011/0282070 A1 | 11/2011 | Shimoharada et al. | |

FOREIGN PATENT DOCUMENTS

| | | |
|---|---|---|
| DE | 199 55 662 A1 | 5/2001 |
| JP | 2004 43397 | 2/2004 |
| WO | 2010 000365 | 1/2010 |
| WO | 2010 067895 | 6/2010 |

OTHER PUBLICATIONS

International Search Report Issued Jan. 31, 2012 in PCT/JP11/74373 Filed Oct. 18, 2011.

*Primary Examiner* — Alton Pryor
(74) *Attorney, Agent, or Firm* — Oblon, Spivak, McClelland, Maier & Neustadt, L.L.P.

(57) ABSTRACT

Many herbicidal compositions have been developed and used, but there are many types of weeds to be controlled, and their development lasts for a long period of time. Accordingly, it has been desired to develop a herbicidal composition having a wider herbicidal spectrum and having a highly active and long-lasting herbicidal activity. The present invention provides a herbicidal composition which comprises as active ingredients (a) at least one herbicidal compound selected from the group consisting of a benzoylpyrazole compound represented by the formula (I): (wherein each of $R^1$, $R^2$, $R^3$, $R^4$ and $R^6$ is alky, and $R^5$ is alkoxyalkoxy), sulcotrione and topramezone, and (b) amicarbazone.

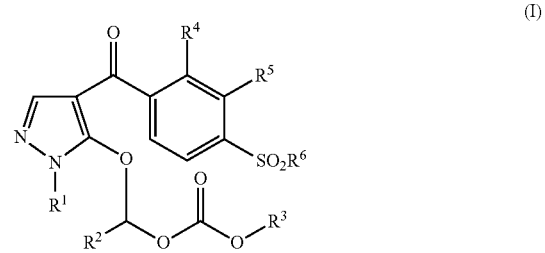

(I)

11 Claims, No Drawings

HERBICIDAL COMPOSITION

TECHNICAL FIELD

The present invention relates to herbicidal compositions.

BACKGROUND ART

Patent Document 1 discloses herbicidal compositions comprising certain herbicidal benzoylpyrazole compounds and various known herbicidal compounds, and discloses amicarbazone as one of the known herbicidal compounds. Patent Document 2 discloses herbicidal compositions comprising amicarbazone and various known herbicidal compounds, and discloses sulcotrione as one of the known herbicidal compounds. Patent Documents 1 and 2 cover the combination according to the herbicidal composition of the present invention as one of many combinations, but these documents do not specifically disclose the herbicidal composition of the present invention.

PRIOR ART DOCUMENTS

Patent Documents

Patent Document 1: WO2010/067895
Patent Document 2: U.S. Pat. No. 5,968,873

DISCLOSURE OF INVENTION

Technical Problem

At present, many herbicidal compositions have been developed and used, but there are a variety of types of weeds to be controlled, and their development lasts for a long period of time. Thus, a high activity and long lasting herbicidal composition having a wider herbicidal spectrum has been desired. Further, in recent years, a technique to reduce the dose of the active ingredient has been desired so as to reduce the environmental load to a place where the herbicide is applied or a periphery thereof.

Solution to Problem

The present inventors have conducted extensive studies to accomplish the above object and as a result, found a highly useful herbicidal composition.

That is, the present invention relates to a herbicidal composition which comprises as active ingredients (a) at least one herbicidal compound selected from the group consisting of a benzoylpyrazole compound represented by the formula (I):

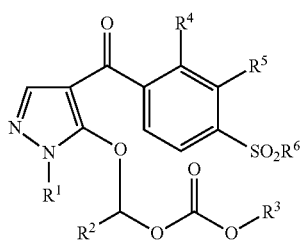

(I)

(wherein each of $R^1$, $R^2$, $R^3$, $R^4$ and $R^6$ is alky, and $R^5$ is alkoxyalkoxy), sulcotrione and topramezone, and (b) amicarbazone. Further, the present invention relates to a method for controlling undesired plants, which comprises applying a herbicidally effective amount of the above herbicidal composition to the undesired plats or to a place where they grow. Further, the present invention relates to a method for controlling undesired plants, which comprises applying a herbicidally effective amount of (a) the herbicidal compound and a herbicidally effective amount of (b) amicarbazone to the undesired plats or to a place where they grow.

ADVANTAGEOUS EFFECTS OF INVENTION

The herbicidal composition of the present invention is capable of controlling a wide range of undesired plants emerging in agricultural fields or non-agricultural fields. It surprisingly presents a synergistic herbicidal effect i.e. a herbicidal effect higher than the mere addition of the respective herbicidal effects of the active ingredients. Such a herbicidal composition of the present invention can be applied at a low dose as compared with a case where the respective active ingredients are applied individually. Thus, it is effective to reduce the environmental load on a place where the composition is applied or a periphery thereof. Further, the herbicidal spectrum will be enlarged, and further the herbicidal effects will last over a long period of time.

When the herbicidal activity in a case where two active ingredients are combined, is larger than the simple sum of the respective herbicidal activities of the two active ingredients (the expected activity), it is called a synergistic effect. The activity expected by the combination of two active ingredients can be calculated as follows (Colby S. R., "Weed", vol. 15, p. 20-22, 1967).

$$E = \alpha + \beta - (\alpha \times \beta \div 100)$$

where α: growth inhibition rate when treated with x (g/ha) of herbicide X,

β: growth inhibition rate when treated with y (g/ha) of herbicide Y,

E: growth inhibition rate expected when treated with x (g/ha) of herbicide X and y (g/ha) of herbicide Y.

That is, when the actual growth inhibition rate (measured value) is larger than the growth inhibition rate by the above calculation (calculated value), the activity by the combination can be regarded as showing a synergistic effect. The herbicidal composition of the present invention shows a synergistic effect when calculated by the above formula.

DESCRIPTION OF EMBODIMENTS

The benzoylpyrazole compound of the formula (I), sulcotrione and topramezone as (a) the herbicidal compound of the present invention are 4-hydroxyphenylpyruvate dioxygenase inhibitor type herbicidal compounds.

In the benzoylpyrazole compound of the formula (I), the alkyl in each of $R^1$, $R^2$, $R^3$, $R^4$ and $R^6$ or the alkyl moiety in $R^5$ may, for example, be $C_{1-9}$ alkyl such as methyl, ethyl, n-propyl, iso-propyl, n-butyl, iso-butyl, sec-butyl, tert-butyl, n-pentyl, iso-pentyl, neopentyl, tert-pentyl, n-hexyl, iso-hexyl, n-heptyl, n-octyl or n-nonyl.

In a case where various structural isomers such as optical isomers exist as the benzoylpyrazole compound of the formula (I), they are, of course, all included in the present invention.

As specific examples of the benzoylpyrazole compound of the formula (I), compounds in Table 1 may be mentioned. However, the herbicidal composition of the present invention is by no means restricted to combinations of such compounds with amicarbazone. In Table 1, No. represents a Compound No., Me represents a methyl group and Et an ethyl group.

TABLE 1

(I)

| No. | $R^1$ | $R^2$ | $R^3$ | $R^4$ | $R^5$ | $R^6$ |
|---|---|---|---|---|---|---|
| 1 | Me | Me | Me | Me | $OCH_2CH_2OMe$ | Me |
| 2 | Me | Me | Et | Me | $OCH_2CH_2OMe$ | Me |
| 3 | Et | Me | Et | Me | $OCH_2CH_2OMe$ | Me |
| 4 | Et | Me | Me | Me | $OCH_2CH_2OMe$ | Me |

Sulcotrione and topramezone as (a) the herbicidal compound and (b) amicarbazone are respectively common names, and their chemical structures are as follows.

TABLE 2

| Common name | Chemical structure |
|---|---|
| Sulcotrione | 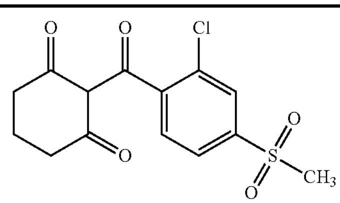 |
| Topramezone | 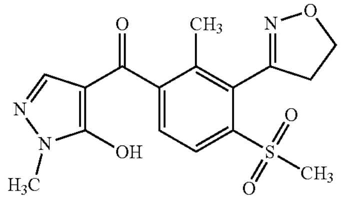 [SMILES: Cc1c(C(=O)c2cnn(C)c2O)ccc(S(C)(=O)=O)c1C1=NOCC1] |
| Amicarbazone | 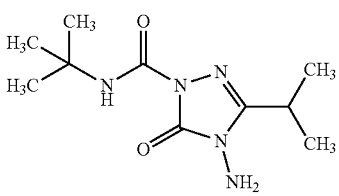 [SMILES: CC(C)c1nn(C(=O)NC(C)(C)C)c(=O)n1N] |

In the present invention, the mixing ratio of (a) the herbicidal compound to (b) amicarbazone cannot generally be defined, as it varies depending upon various conditions such as the type of the compounds to be mixed, the type of the formulation, the weather conditions, and the type and the growth state of the plants to be controlled, but it is from 1:3,000 to 1,000:1, preferably from 1:200 to 150:1, more preferably from 1:55 to 63:1 by the weight ratio of (a):(b).

For example, in a case where (a) the herbicidal compound is the benzoylpyrazole compound of the formula (I), the mixing ratio to (b) amicarbazone is from 1:3,000 to 1,000:1, preferably from 1:200 to 100:1, more preferably from 1:50 to 33:1 by the weight ratio of (a):(b).

For example, in a case where (a) the herbicidal compound is sulcotrione, the mixing ratio to (b) amicarbazone is from 1:3,000 to 1,000:1, preferably from 1:200 to 150:1, more preferably from 1:55 to 63:1 by the weight ratio of (a):(b).

For example, in a case where (a) the herbicidal compound is topramezone, the mixing ratio to (b) amicarbazone is from 1:3,000 to 1,000:1, preferably from 1:200 to 100:1, more preferably from 1:50 to 33:1 by the weight ratio of (a):(b).

The dose of (a) the herbicidal compound and (b) amicarbazone in the present invention cannot generally be defined, as it varies depending upon various conditions such as the types of the compounds to be mixed, the type of the formulation, the weather conditions, and the type and the growth state of the plants to be controlled. However, (a) the herbicidal compound is applied in an amount of from 1 to 1,000 g/ha, preferably from 5 to 750 g/ha, more preferably from 10 to 500 g/ha, and (b) amicarbazone is applied in an amount of from 1 to 3,000 g/ha, preferably from 5 to 1,000 g/ha, more preferably from 8 to 1,000 g/ha.

For example, in a case where (a) the herbicidal compound is the benzoylpyrazole compound of the formula (I), (a) the herbicidal compound is applied in an amount of from 1 to 1,000 g/ha, preferably from 5 to 500 g/ha, more preferably from 10 to 500 g/ha, and (b) amicarbazone is applied in an amount of from 1 to 3,000 g/ha, preferably from 5 to 1,000 g/ha, more preferably from 10 to 750 g/ha.

For example, in a case where (a) the herbicidal compound is sulcotrione, (a) the herbicidal compound is applied in an amount of from 1 to 1,000 g/ha, preferably from 5 to 750 g/ha, more preferably from 10 to 500 g/ha, and (b) amicarbazone is applied in an amount of from 1 to 3,000 g/ha, preferably from 5 to 1,000 g/ha, more preferably from 8 to 1,000 g/ha.

For example, in a case where (a) the herbicidal compound is topramezone, (a) the herbicidal compound is applied in an amount of from 1 to 1,000 g/ha, preferably from 5 to 500 g/ha, more preferably from 10 to 500 g/ha, and (b) amicarbazone is applied in an amount of from 1 to 3,000 g/ha, preferably from 5 to 1,000 g/ha, more preferably from 10 to 750 g/ha.

The herbicidal composition of the present invention has excellent herbicidal effects. The application range extends to crop plant fields, orchards and plantation. The application method may suitably be selected from soil application, foliar application, soil incorporation, etc.

The herbicidal composition of the present invention are capable of controlling a wide range of undesired weeds, such as gramineae such as barnyardgrass (*Echinochloa crus-galli* L., *Echinochloa oryzicola* vasing.), crabgrass (*Digitaria sanquinalis* L., *Digitaria ischaemum* Muhl., *Digitaria adscendens* Henr., *Digitaria microbachne* Henr., *Digitaria horizontalis* Willd.), green foxtail (*Setaria viridis* L.), giant foxtail (*Setaria faberi* Herrm.), yellow foxtail (*Setaria lutescens* Hubb.), goosegrass (*Eleusine indica* L.), wild oat (*Avena fatua* L.), johnsongrass (*Sorghum halepense* L.), quackgrass (*Agropyron repens* L.), alexandergrass (*Brachiaria plantaginea*), guineagrass (*Panicum maximum* Jacq.), paragrass (*Panicum purpurascens*), sprangletop (*Leptochloa chinensis*), red sprangletop (*Leptochloa panicea*), annual bluegrass (*Poa annua* L.), black grass (*Alopecurus myosuroides* Huds.), cholorado bluestem (*Agropyron tsukushiense* (Honda) Ohwi), broadleaf signalgrass (*Brachiaria platyphylla* Nash), southern sandbur (*Cenchrus echinatus* L.), italian ryegrass (*Lolium multiflorum* Lam.), and bermudagrass (*Cynodon dactylon* Pers.); cyperaceae such as rice flatsedge (*Cyperus iria* L.), purple nutsedge (*Cyperus rotundus* L.), yellow nutsedge (*Cyperus esculentus* L.), Japanese bulrush (*Scirpus juncoides*), flatsedge (*Cyperus serotinus*), small-flower umbrellaplant (*Cyperus difformis*), slender spikerush (*Eleocharis acicularis), and water chestnut (*Eleocharis kuroguwai*); alismataceae such as Japanese ribbon waparo (*Sagittaria pygmnaea*), arrow-head (*Sagittaria trifolia*), and narrowleaf waterplantain (*Alisma canaliculatum*); pontederiaceae such as monochoria (*Monochoria vaginalis*), and monochoria species (*Monochoria korsakowii*); scrophulariaceae such as false pimpernel (*Lindernia pyxidaria*), and abunome (*Dopatrium junceum*); lythraceae such as toothcup (*Rotala india*), and red stem (*Ammannia multiflora*); elatinaceae such as long stem waterwort (*Elatine triandra* SCHK.); malvaceae such as velvetleaf (*Abutilon theophrasti* MEDIC.), and prickly sida (*Sida spinosa* L.); compositae such as common cocklebur (*Xanthium strumarium* L.), common ragweed (*Ambrosia elatior* L.), thistle (*Breea setosa* (BIEB.) KITAM.), hairy galinsoga (*Galinsoga ciliata* Blake), wild chamomile (*Matricaria chamomilla* L.); solanaceae such as black nightshade (*Solanum nigrum* L.), and jimsonweed (*Datura stramonium*); amaranthaceae such as slender amaranth (*Amaranthus viridis* L.), and redroot pigweed (*Amaranthus retroflexus* L.); polygonaceeae such as pale smartweed (*Polygonum lapathifolium* L.), ladysthumb (*Polygonum persicaria* L.), wild buckwheat (*Polygonum convolvulus* L.), and knotweed (*Polygonum aviculare* L.); cruciferae such as flexuous bittercress (*Cardamine flexuosa* WITH.), shepherd's-purse (*Capsella bursa-pastoris* Medik.), and indian mustard (*Brassica juncea* Czern.); convolvulaceae such as tall morningglory (*Ipomoea purpurea* L.), field bindweed (*Convolvulus arvensis* L.), and ivyleaf morningglory (*Ipomoea hederacea* Jacq.); Chenopodiaceae such as common lambsquarters (*Chenopodium album* L.), and mexican burningbush (*Kochia scoparia* Schrad.); Portulacaceae such as common purslane (*Portulaca oleracea* L.); leguminosae such as sicklepod (*Cassia obtusifolia* L.); caryophyllaceae such as common chickweed (*Stellaria media* L.); labiatae such as henbit (*Lamium amplexicaule* L.); rubiaceae such as catchweed (*Galium spurium* L.); euphorbiaceae such as threeseeded copperleaf (*Acalypha australis* L.); and Commelinaceae such as common dayflower (*Commelina communis* L.).

Therefore, they can be effectively used for selectively controlling noxious weeds in cultivation of useful crops such as corn (*Zea mays* L.), soybean (*Glycine max* Merr.), cotton (*Gossypium* spp.), wheat (*Triticum* spp.), rice (*Oryza sativa* L.), barley (*Hordeum vulgare* L.), rye (*Secale cereale* L.), oat (*Avena sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), japanese lawnqrass (*Zoysia japonica* stend), peanut (*Arachis hypogaea* L.), flax (*Linum usitatissimum* L.), tobacco (*Nicotiana tabacum* L.), and coffee (*Coffea* spp.). Particularly, the herbicidal composition of the present invention are effectively used for selectively controlling noxious weeds in cultivation of corn, wheat, sugar cane, and the like. And the herbicidal composition of the present invention can be effectively used for nonselectively controlling noxious weeds.

The herbicidal composition of the present invention is effectively used to selectively control noxious weeds in cultivation of various transformed plants. Examples of the transformed plants include pest-resistant transformed plants, phytopathogen-resistant transformed plants, transformed plants regarding plant components, and herbicide-tolerant transformed plants.

The herbicidal composition of the present invention exhibits remarkable synergistic effects, whereby particularly the dose of amicarbazone can be reduced. As a result, undesired effects of amicarbazone over corn can be reduced and in addition, surprisingly, controlling activity against various noxious weeds is sufficiently maintained, and thus the herbicidal composition of the present invention is very useful in the practical application. Further, the herbicidal composition of the present invention has remarkable residual activity. Still further, the herbicidal composition of the present invention can control climbing weeds such as tall morningglory, field bindweed and ivyleaf morningglory which are considered to be strong noxious weeds in corn fields, and is thereby very useful in the practical application.

In the present invention, in addition to (a) the herbicidal compound and (b) amicarbazone, as the case requires, other herbicidal compounds may be used as mixed. Such other herbicidal compounds can optionally be selected from various known herbicidal compounds considering the application site of the herbicidal composition, and the type and the growth state of the plants to be controlled. Further, the herbicidal composition of the present invention may be mixed with or may be used in combination with fungicides, antibiotics, plant hormones, insecticides, fertilizers, phytotoxicity-reducing agents, etc, whereby more excellent effects and activity may be obtained. Other herbicidal compounds include, for example, the following compounds (by common names), and one or more may suitably be selected. Even when not specifically mentioned here, in a case where such compounds have salts, alkyl esters, hydrates, different crystal forms, various structural isomers, etc., they are, of course, all included.

(1) Those which are believed to exhibit herbicidal effects by disturbing hormone activities of plants, such as a phenoxy type such as 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide or clomeprop; an aromatic carboxylic acid type such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium or aminopyralid; and others such as naptalam, naptalam-sodium, benazolin, benazolin-ethyl, quinclorac, quinmerac, diflufenzopyr, diflufenzopyr-sodium, fluoroxypyr, fluoroxypyr-2-butoxy-1-methylethyl, fluoroxypyr-meptyl, chlorflurenol or chlorflurenol-methyl.

(2) Those which are believed to exhibit herbicidal effects by inhibiting photosynthesis of plants, such as a urea type such as chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton or trietrazine; a triazine type such as simazine, atrazine, atratone, simetryn, prometryn, dimethametryn, hexazinone, metribuzin, terbuthylazine, cyanazine, ametryn, cybutryne, triaziflam, indaziflam, terbutryn, propazine, metamitron or prometon; a uracil type such as bromacil, bromacyl-lithium, lenacil or terbacil; an anilide type such as propanil or cypromid; a carbamate type such as swep, desmedipham or phenmedipham; a hydroxybenzonitrile type such as bromoxynil, bromoxynil-octanoate, bromoxynil-heptanoate, ioxynil, ioxynil-octanoate, ioxynil-potassium or ioxynil-sodium; and others such as pyridate, bentazone, bentazone-sodium, methazole or pentanochlor.

(3) Quaternary ammonium salt type such as paraquat or diquat, which is believed to be converted to free radicals by itself to form active oxygen in the plant body and shows rapid herbicidal efficacy.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen, acifluorfen-sodium, fomesafen, fomesafen-sodium, oxyfluorfen, lactofen, aclonifen, ethoxyfen-ethyl (HC-252), fluoroglycofen-ethyl or fluoroglycofen; a cyclic imide type such as chlorphthalim, flumioxazin, flumiclorac, flumiclorac-pentyl, cinidon-ethyl or fluthiacet-methyl; and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, flupoxam, fluazolate, profluazol, pyraclonil, flufenpyr-ethyl or bencarbazone.

(5) Those which are believed to exhibit herbicidal effects characterized by bleaching activities by inhibiting chromogenesis of plants such as carotenoids, such as a pyridazinone type such as norflurazon, chloridazon or metflurazon; a pyrazole type such as pyrazolynate, pyrazoxyfen, benzofenap, topramezone or pyrasulfotole; and others such as amitrole, fluridone, flurtamone, diflufenican, methoxyphenone, clomazone, sulcotrione, mesotrione, tembotrione, tefurytrione (AVH-301), bicyclopyrone, isoxaflutole, difenzoquat, difenzoquat-metilsulfate, isoxachlortole, benzobicyclon, picolinafen or beflubutamid.

(6) Those which exhibit strong herbicidal effects specifically to gramineous plants, such as an aryloxyphenoxypropionic acid type such as diclofop-methyl, diclofop, pyriphenop-sodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop or propaquizafop; a cyclohexanedione type such as alloxydim-sodium, alloxydim, clethodim, sethoxydim, tralkoxydim, butroxydim, tepraloxydim, profoxydim or cycloxydim; and others such as flamprop-M-methyl, flamprop-M or flamprop-M-isopropyl.

(7) Those which are believed to exhibit herbicidal effects by inhibiting an amino acid biosynthesis of plants, such as a sulfonylurea type such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, flazasulfuron, rimsulfuron, nicosulfuron, imazosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, flucetosulfuron, amidosulfuron, propyrisulfuron (TH-547), metazosulfuron, or a compound disclosed in the claim of WO2005092104; a triazolopyrimidinesulfonamide type such as flumetsulam, metosulam, diclosulam, cloransulam-methyl, florasulam, penoxsulam or pyroxsulam; an imidazolinone type such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl or imazapic; a pyrimidinylsalicylic acid type such as pyrithiobac-sodium, bispyribac-sodium, pyriminobac-methyl, pyribenzoxim, pyriftalid or pyrimisulfan; a sulfonylaminocarbonyltriazolinone type such as flucarbazone, flucarbazone-sodium, propoxycarbazone-sodium or propoxycarbazone; and others such as glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium or cinmethylin.

(8) Those which are believed to exhibit herbicidal effects by inhibiting cell mitoses of plants, such as a dinitroaniline type such as trifluralin, oryzalin, nitralin, pendimethalin, ethalfluralin, benfluralin, prodiamine, butralin or dinitramine; an amide type such as bensulide, napropamide, propyzamide or pronamide; an organic phosphorus type such as amiprofos-methyl, butamifos, anilofos or piperophos; a phenyl carbamate type such as propham, chlorpropham, barban or carbetamide; a cumylamine type such as daimuron, cumyluron, bromobutide or methyldymron; and others such as asulam, asulam-sodium, dithiopyr, thiazopyr, chlorthal-dimethyl, chlorthal or diphenamid.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachior, dimethenamid, dimethenamid-P, propisochloror dimethachlor; a thiocarbamate type such as molinate, dimepiperate, pyributicarb, EPTC, butylate, vernolate, pebulate, cycloate, prosulfocarb, esprocarb, thiobencarb, diallate, tri-allate or orbencarb; and others such as etobenzanid, mefenacet, flufenacet, tridiphane, cafenstrole, fentrazamide, oxaziclomefone, indanofan, benfuresate, pyroxasulfone, fenoxasulfone, dalapon, dalapon-sodium, TCA-sodium or trichloroacetic acid.

(10) MSMA, DSMA, CMA, endothall, endothall-dipotassium, endothall-sodium, endothall-mono(N,N-dimethylalkylammonium), ethofumesate, sodium chlorate, pelargonic acid (nonanoic acid), fosamine, fosamine-ammonium, pinoxaden, ipfencarbazone (HOK-201), aminocyclopyrachlor, aminocyclopyrachlor-methyl, aminocyclopyrachlor-potassium, aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, etc.

(11) Those which are believed to exhibit herbicidal effects by being parasitic on plants, such as *Xanthomonas campestris, Epicoccisirus nematosorus, Epicoccosirus nematosperus, Exserohilum monoseras* or *Drechsrela monoceras*.

With respect to application of the herbicidal composition of the present invention, application to undesired plants or application to a place where they grow (either before or after emerging of the plants) may optionally be selected. Further, (a) the herbicidal compound and (b) amicarbzaone may separately be formulated so that they are mixed for use at the time of application, or they may be formulated together. As examples of a specific application method, the following may be mentioned.

1. (a) The herbicidal compound and (b) amicarbazone are formulated together, and the formulation is applied as it is.
2. (a) The herbicidal compound and (b) amicarbazone are formulated together, the formulation is diluted to a predetermined concentration with e.g. water, and as the case requires, a spreader (such as a surfactant, a vegetable oil or a mineral oil) is added for application.
3. (a) The herbicidal compound and (b) amicarbazone are separately formulated and applied as they are.
4. (a) The herbicidal compound and (b) amicarbazone are separately formulated, and they are diluted to a predetermined concentration with e.g. water, and as the case requires, a spreader (such as a surfactant, a vegetable oil or a mineral oil) is added for application.
5. (a) The herbicidal compound and (b) amicarbazone are separately formulated, and the formulations are mixed when diluted to a predetermined concentration with e.g. water, and as the case requires, a spreader (such as a surfactant, a vegetable oil or a mineral oil) is added for application.

The herbicidal composition of the present invention may be prepared by mixing (a) the herbicidal compound and (b) amicarbazone, as active ingredients, with various agricultural additives in accordance with conventional formulation methods for agricultural chemicals, and applied in the form of various formulations such as dusts, granules, water dispersible granules, wettable powders, tablets, pills, capsules (including a formulation packaged by a water soluble film), water-based suspensions, oil-based suspensions, microemulsions, suspoemulsions, water soluble powders, emulsifiable concentrates, soluble concentrates or pastes. It may be formed into any formulation which is commonly used in this field, so long as the object of the present invention is thereby met.

At the time of the formulation, (a) the herbicidal compound and (b) amicarbazone may be mixed together for the formulation, or they may be separately formulated.

The additives to be used for the formulation include, for example, a solid carrier such as diatomaceous earth, slaked lime, calcium carbonate, talc, white carbon, kaoline, bentonite, kaolinite, sericite, clay, sodium carbonate, sodium bicarbonate, mirabilite, zeolite or starch; a solvent such as water, toluene, xylene, solvent naphtha, dioxane, acetone, isophorone, methyl isobutyl ketone, chlorobenzene, cyclohexane, dimethylsulfoxide, dimethylformamide, dimethylacetamide, N-methyl-2-pyrrolidone or an alcohol; an anionic surfactant or spreader such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenylether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonate condensed with formaldehyde or an alkylnaphthalene sulfonate condensed with formaldehyde; a nonionic surfactant or spreader such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; and a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins. These additives may suitably be selected for use alone or in combination as a mixture of two or more of them, so long as the object of the present invention is met. Further, additives other than the above-mentioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight of (a) the herbicidal compound or (b) amicarbazone to such various additives may be from 0.1:99.9 to 95:5, preferably from 0.2:99.8 to 85:15.

Now, examples of preferred embodiments of the present invention will be given below, but it should be understood that the present invention is by no means restricted thereto.

(1) The above herbicidal composition wherein (a) the herbicidal compound is a benzoylpyrazole compound of the formula (I).

(2) The herbicidal composition according to the above (1) wherein in the formula (I), each of $R^1$, $R^2$, $R^3$, $R^4$ and $R^6$ is methyl or ethyl, and $R^5$ is —$OCH_2CH_2OCH_3$.

(3) The herbicidal composition according to the above (1) wherein in the formula (I), each of $R^1$ and $R^3$ is methyl or ethyl, each of $R^2$, $R^4$ and $R^6$ is methyl, and $R^5$ is —$OCH_2CH_2OCH_3$.

(4) The herbicidal composition according to the above (1), wherein the benzoylpyrazole compound of the formula (I) is Compound No. 1, 2, 3 or 4 in Table 1.

(5) The above herbicidal composition wherein (a) the herbicidal compound is sulcotrione.

(6) The above herbicidal composition wherein (a) the herbicidal compound is topramezone.

(7) The above herbicidal composition wherein (a) the herbicidal compound is at least one herbicidal compound selected from the group consisting of a benzoylpyrazole compound of the formula (I) and topramezone.

(8) A method for controlling undesired plants, which comprises applying a herbicidally effective amount of the herbicidal composition as defined in any one of the above (1) to (7) to the undesired plants or to a place where they grow.

(9) A method for controlling undesired plants, which comprises applying a herbicidally effective amount of (a) a benzoylpyrazole compound of the formula (I) and a herbicidally effective amount of (b) amicarbazone to the undesired plants or to a place where they grow.

(10) The method according to the above (9) wherein in the formula (I), each of $R^1$, $R^2$, $R^3$, $R^4$ and $R^6$ is methyl or ethyl, and $R^5$ is —$OCH_2CH_2OCH_3$.

(11) The method according to the above (9), wherein in the formula (I), each of $R^1$ and $R^3$ is methyl or ethyl, each of $R^2$, $R^4$ and $R^6$ is methyl, and $R^5$ is —$OCH_2CH_2OCH_3$.

(12) The method according to the above (9), wherein the benzoylpyrazole compound of the formula (I) is Compound No. 1, 2, 3 or 4 in Table 1.

(13) A method for controlling undesired plants, which comprises applying a herbicidally effective amount of (a) sulcotrione and a herbicidally effective amount of (b) amicarbazone to the undesired plants or to a place where they grow.

(14) A method for controlling undesired plants, which comprises applying a herbicidally effective amount of (a) topramezone and a herbicidally effective amount of (b) amicarbazone to the undesired plants or to a place where they grow.

(15) A method for controlling undesired plants, which comprises applying a herbicidally effective amount of (a) at least one herbicidal compound selected from the group consisting of a benzoylpyrazole compound of the formula (I) and topramezone, and a herbicidally effective amount of (b) amicarbazone to the undesired plants or to a place where they grow.

EXAMPLES

Now, the present invention will be described in further detail with reference to Examples. However, it should be understood that the present invention is by no means restricted to such specific Examples.

Example 1

Upland field soil was put into a 1/1,000,000 hectare pot, and seeds of various plants (barnyardgrass (*Echinochloa crus-galli* L.) and velvetleaf (*Abutilon theophrasti* MEDIC.) were sown. When the respective plants reached predetermined leaf stage, herbicidal compositions in predetermined amounts were diluted with water in an amount corresponding to 300 L/ha and applied for foliar treatment by a small sprayer.

On the 8 to 14 days after treatment (DAT), the state of growth of the respective plants was visually observed to determine the growth inhibition rate (measured value) in accordance with the following evaluation standard. Further, in accordance with the Colby's formula, the growth inhibition rate (calculated value) was calculated. The results are shown in Tables 2-1 to 2-13. In Tables, with respect to the benzoylpyrazole compound represented by the formula (I), Compound Nos. in Table 1 are described, and with respect to other compounds, common names are described.

Growth inhibition rate (%)=0: equivalent to the non-treated area to 100: complete kill

TABLE 2-1

| Compound | Active ingredient amount (g/ha) | Growth inhibition rate (%) of barnyardgrass (2.8 to 3.4 leaf stage): 8 DAT | |
|---|---|---|---|
| | | Measured value | Calculated value |
| No. 1 | 7 | 75 | — |
| | 15 | 73 | — |
| Amicarbazone | 18.75 | 30 | — |
| | 37.5 | 50 | — |
| No. 1 + Amicarbazone | 7 + 18.75 | 95 | 82.5 |
| | 7 + 37.5 | 98 | 87.5 |
| | 15 + 18.75 | 97 | 81.1 |
| | 15 + 37.5 | 98 | 86.5 |

TABLE 2-2

| Compound | Active ingredient amount (g/ha) | Growth inhibition rate (%) of velvetleaf (1.8 to 2.4 leaf stage): 8 DAT | |
|---|---|---|---|
| | | Measured value | Calculated value |
| No. 1 | 7 | 30 | — |
| | 15 | 30 | — |
| Amicarbazone | 18.75 | 40 | — |
| | 37.5 | 45 | — |
| No. 1 + Amicarbazone | 7 + 18.75 | 78 | 58.0 |
| | 7 + 37.5 | 80 | 61.5 |
| | 15 + 18.75 | 78 | 58.0 |
| | 15 + 37.5 | 75 | 61.5 |

TABLE 2-3

| Compound | Active ingredient amount (g/ha) | Growth inhibition rate (%) of barnyardgrass (3.6 to 4.5 leaf stage): 8 DAT | |
|---|---|---|---|
| | | Measured value | Calculated value |
| No. 2 | 7 | 45 | — |
| | 15 | 50 | — |
| Amicarbazone | 18.75 | 20 | — |
| | 37.5 | 25 | — |
| No. 2 + Amicarbazone | 7 + 18.75 | 88 | 56.0 |
| | 7 + 37.5 | 93 | 58.7 |
| | 15 + 18.75 | 83 | 60.0 |
| | 15 + 37.5 | 88 | 62.5 |

TABLE 2-4

| Compound | Active ingredient amount (g/ha) | Growth inhibition rate (%) of velvetleaf (2.6 to 3.2 leaf stage): 8 DAT | |
|---|---|---|---|
| | | Measured value | Calculated value |
| No. 2 | 7 | 30 | — |
| | 15 | 30 | — |
| Amicarbazone | 18.75 | 50 | — |
| | 37.5 | 60 | — |
| No. 2 + Amicarbazone | 7 + 18.75 | 83 | 65.0 |
| | 7 + 37.5 | 85 | 72.0 |
| | 15 + 18.75 | 80 | 65.0 |
| | 15 + 37.5 | 85 | 72.0 |

TABLE 2-5

| Compound | Active ingredient amount (g/ha) | Growth inhibition rate (%) of barnyardgrass (2.8 to 3.4 leaf stage): 8 DAT | |
|---|---|---|---|
| | | Measured value | Calculated value |
| No. 3 | 7 | 68 | — |
| | 15 | 75 | — |
| Amicarbazone | 18.75 | 30 | — |
| | 37.5 | 50 | — |
| No. 3 + Amicarbazone | 7 + 18.75 | 97 | 77.6 |
| | 7 + 37.5 | 95 | 84.0 |
| | 15 + 18.75 | 97 | 82.5 |
| | 15 + 37.5 | 97 | 87.5 |

TABLE 2-6

| Compound | Active ingredient amount (g/ha) | Growth inhibition rate (%) of velvetleaf (1.8 to 2.4 leaf stage): 8 DAT Measured value | Calculated value |
|---|---|---|---|
| No. 3 | 7 | 30 | — |
|  | 15 | 35 | — |
| Amicarbazone | 18.75 | 40 | — |
|  | 37.5 | 45 | — |
| No. 3 | 7 + 18.75 | 80 | 58.0 |
| + | 7 + 37.5 | 85 | 61.5 |
| Amicarbazone | 15 + 18.75 | 75 | 61.0 |
|  | 15 + 37.5 | 80 | 64.2 |

TABLE 2-7

| Compound | Active ingredient amount (g/ha) | Growth inhibition rate (%) of barnyardgrass (4.2 to 5.3 leaf stage): 14 DAT Measured value | Calculated value |
|---|---|---|---|
| No. 4 | 7 | 85 | — |
|  | 15 | 90 | — |
| Amicarbazone | 30 | 0 | — |
|  | 50 | 0 | — |
|  | 75 | 15 | — |
| No. 4 | 7 + 30 | 99 | 85.0 |
| + | 7 + 50 | 100 | 85.0 |
| Amicarbazone | 7 + 75 | 99 | 87.2 |
|  | 15 + 30 | 100 | 90.0 |
|  | 15 + 50 | 100 | 90.0 |
|  | 15 + 75 | 100 | 91.5 |

TABLE 2-8

| Compound | Active ingredient amount (g/ha) | Growth inhibition rate (%) of barnyardgrass (3.2 to 4.1 leaf stage): 11 DAT Measured value | Calculated value |
|---|---|---|---|
| No. 4 | 7 | 80 | — |
|  | 15 | 85 | — |
| Amicarbazone | 75 | 40 | — |
|  | 150 | 73 | — |
| No. 4 | 7 + 75 | 99 | 88.0 |
| + | 7 + 150 | 99 | 94.6 |
| Amicarbazone | 15 + 75 | 98 | 91.0 |
|  | 15 + 150 | 100 | 95.9 |

TABLE 2-9

| Compound | Active ingredient amount (g/ha) | Growth inhibition rate (%) of velvetleaf (4 to 4.5 leaf stage): 14 DAT Measured value | Calculated value |
|---|---|---|---|
| No. 4 | 7 | 75 | — |
|  | 15 | 80 | — |
| Amicarbazone | 30 | 35 | — |
|  | 50 | 55 | — |
|  | 75 | 55 | — |
| No. 4 | 7 + 30 | 97 | 83.7 |
| + | 7 + 50 | 97 | 88.7 |
| Amicarbazone | 7 + 75 | 100 | 88.7 |
|  | 15 + 30 | 100 | 87.0 |

TABLE 2-9-continued

| Compound | Active ingredient amount (g/ha) | Growth inhibition rate (%) of velvetleaf (4 to 4.5 leaf stage): 14 DAT Measured value | Calculated value |
|---|---|---|---|
|  | 15 + 50 | 100 | 91.0 |
|  | 15 + 75 | 100 | 91.0 |

TABLE 2-10

| Compound | Active ingredient amount (g/ha) | Growth inhibition rate (%) of barnyardgrass (3.6 to 4.5 leaf stage): 8 DAT Measured value | Calculated value |
|---|---|---|---|
| Sulcotrione | 75 | 40 | — |
|  | 150 | 45 | — |
| Amicarbazone | 18.75 | 20 | — |
|  | 37.5 | 25 | — |
| Sulcotrione | 75 + 18.75 | 90 | 52.0 |
| + | 75 + 37.5 | 90 | 55.0 |
| Amicarbazone | 150 + 18.75 | 90 | 56.0 |
|  | 150 + 37.5 | 93 | 58.7 |

TABLE 2-11

| Compound | Active ingredient amount (g/ha) | Growth inhibition rate (%) of velvetleaf (2.6 to 3.2 leaf stage): 8 DAT Measured value | Calculated value |
|---|---|---|---|
| Sulcotrione | 75 | 30 | — |
|  | 150 | 30 | — |
| Amicarbazone | 18.75 | 50 | — |
|  | 37.5 | 60 | — |
| Sulcotrione | 75 + 18.75 | 80 | 65.0 |
| + | 75 + 37.5 | 83 | 72.0 |
| Amicarbazone | 150 + 18.75 | 83 | 65.0 |
|  | 150 + 37.5 | 85 | 72.0 |

TABLE 2-12

| Compound | Active ingredient amount (g/ha) | Growth inhibition rate (%) of barnyardgrass (3.6 to 4.5 leaf stage): 8 DAT Measured value | Calculated value |
|---|---|---|---|
| Topramezone | 7 | 40 | — |
|  | 15 | 40 | — |
| Amicarbazone | 18.75 | 20 | — |
|  | 37.5 | 25 | — |
| Topramezone | 7 + 18.75 | 88 | 52.0 |
| + | 7 + 37.5 | 93 | 55.0 |
| Amicarbazone | 15 + 18.75 | 85 | 52.0 |
|  | 15 + 37.5 | 90 | 55.0 |

TABLE 2-13

| Compound | Active ingredient amount (g/ha) | Growth inhibition rate (%) of velvetleaf (2.6 to 3.2 leaf stage): 8 DAT | |
|---|---|---|---|
| | | Measured value | Calculated value |
| Topramezone | 7 | 30 | — |
| | 15 | 30 | — |
| Amicarbazone | 18.75 | 50 | — |
| | 37.5 | 60 | — |
| Topramezone + Amicarbazone | 7 + 18.75 | 80 | 65.0 |
| | 7 + 37.5 | 85 | 72.0 |
| | 15 + 18.75 | 75 | 65.0 |
| | 15 + 37.5 | 85 | 72.0 |

Example 2

In accordance with the above Example 1, herbicidal tests with compounds and active ingredient amounts as illustrated in Table 3 against various plants (barnyardgrass (*Echinochloa crus-galli* L.), velvetleaf (*Abutilon theophrasti* MEDIC.) crabgrass (*Diqitaria sanguinalis* L.), and common ragweed (*Ambrosia elatior* L.)) are carried out, whereupon the herbicidal compositions of the present invention show favorable growth inhibition effects (e.g. synergistic effect). In Table 3, with respect to the benzoylpyrazole compound represented by the formula (I), Compound Nos. in Table 1 are described, and with respect to other compounds, common names are described.

TABLE 3

| | (a) Herbicidal compound | | Active ingredient amount of (b) amicarbazone (g/ha) |
|---|---|---|---|
| | Compound | Active ingredient amount (g/ha) | |
| 1 | No. 1 | 15 | 15 |
| | | 15 | 63 |
| | | 15 | 250 |
| | | 15 | 750 |
| | | 30 | 15 |
| | | 30 | 63 |
| | | 30 | 250 |
| | | 30 | 750 |
| | | 50 | 15 |
| | | 50 | 63 |
| | | 50 | 250 |
| | | 50 | 750 |
| | | 100 | 15 |
| | | 100 | 63 |
| | | 100 | 250 |
| | | 100 | 750 |
| | | 500 | 15 |
| | | 500 | 63 |
| | | 500 | 250 |
| | | 500 | 750 |
| 2 | No. 2 | 15 | 15 |
| | | 15 | 63 |
| | | 15 | 250 |
| | | 15 | 750 |
| | | 30 | 15 |
| | | 30 | 63 |
| | | 30 | 250 |
| | | 30 | 750 |
| | | 50 | 15 |
| | | 50 | 63 |
| | | 50 | 250 |
| | | 50 | 750 |
| | | 100 | 15 |
| | | 100 | 63 |
| | | 100 | 250 |

TABLE 3-continued

| | (a) Herbicidal compound | | Active ingredient amount of (b) amicarbazone (g/ha) |
|---|---|---|---|
| | Compound | Active ingredient amount (g/ha) | |
| | | 100 | 750 |
| | | 500 | 15 |
| | | 500 | 63 |
| | | 500 | 250 |
| | | 500 | 750 |
| 3 | No. 3 | 15 | 15 |
| | | 15 | 63 |
| | | 15 | 250 |
| | | 15 | 750 |
| | | 30 | 15 |
| | | 30 | 63 |
| | | 30 | 250 |
| | | 30 | 750 |
| | | 50 | 15 |
| | | 50 | 63 |
| | | 50 | 250 |
| | | 50 | 750 |
| | | 100 | 15 |
| | | 100 | 63 |
| | | 100 | 250 |
| | | 100 | 750 |
| | | 500 | 15 |
| | | 500 | 63 |
| | | 500 | 250 |
| | | 500 | 750 |
| 4 | No. 4 | 15 | 15 |
| | | 15 | 63 |
| | | 15 | 250 |
| | | 15 | 750 |
| | | 30 | 15 |
| | | 30 | 63 |
| | | 30 | 250 |
| | | 30 | 750 |
| | | 50 | 15 |
| | | 50 | 63 |
| | | 50 | 250 |
| | | 50 | 750 |
| | | 100 | 15 |
| | | 100 | 63 |
| | | 100 | 250 |
| | | 100 | 750 |
| | | 500 | 15 |
| | | 500 | 63 |
| | | 500 | 250 |
| | | 500 | 750 |
| 5 | Sulcotrione | 18.8 | 8 |
| | | 18.8 | 40 |
| | | 18.8 | 200 |
| | | 18.8 | 1000 |
| | | 75 | 8 |
| | | 75 | 40 |
| | | 75 | 200 |
| | | 75 | 1000 |
| | | 300 | 8 |
| | | 300 | 40 |
| | | 300 | 200 |
| | | 300 | 1000 |
| | | 500 | 8 |
| | | 500 | 40 |
| | | 500 | 200 |
| | | 500 | 1000 |
| 6 | Topramezone | 15 | 15 |
| | | 15 | 63 |
| | | 15 | 250 |
| | | 15 | 750 |
| | | 30 | 15 |
| | | 30 | 63 |
| | | 30 | 250 |
| | | 30 | 750 |
| | | 50 | 15 |
| | | 50 | 63 |
| | | 50 | 250 |
| | | 50 | 750 |
| | | 100 | 15 |

TABLE 3-continued

| (a) Herbicidal compound | | |
|---|---|---|
| Compound | Active ingredient amount (g/ha) | Active ingredient amount of (b) amicarbazone (g/ha) |
| | 100 | 63 |
| | 100 | 250 |
| | 100 | 750 |
| | 500 | 15 |
| | 500 | 63 |
| | 500 | 250 |
| | 500 | 750 |

The entire disclosure of Japanese Patent Application No. 2010-237558 filed on Oct. 22, 2010 including specification, claims and summary is incorporated herein by reference in its entirety.

The invention claimed is:

1. A synergistic herbicidal composition which comprises as active ingredients (a) at least one herbicidal compound selected from the group consisting of a benzoylpyrazole compound represented by the formula (I):

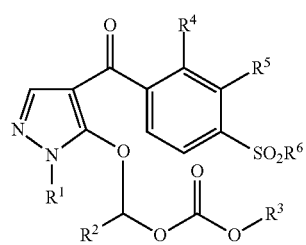

(wherein each of $R^1$, $R^2$, $R^3$, $R^4$ and $R^6$ is alky, and $R^5$ is alkoxyalkoxy), sulcotrione and topramezone, and (b) amicarbazone.

2. The herbicidal composition according to claim 1, wherein (a) the herbicidal compound is at least one herbicidal compound selected from the group consisting of a benzoylpyrazole compound represented by the formula (I) and topramezone.

3. The herbicidal composition according to claim 1, wherein (a) the herbicidal compound is a benzoylpyrazole compound represented by the formula (I).

4. The herbicidal composition according to claim 3, wherein in the formula (I), each of $R^1$, $R^2$, $R^3$, $R^4$ and $R^6$ is methyl or ethyl, and $R^5$ is —$OCH_2CH_2OCH_3$.

5. The herbicidal composition according to claim 3, wherein in the formula (I), each of $R^1$ and $R^3$ is methyl or ethyl, each of $R^2$, $R^4$ and $R^6$ is methyl, and $R^5$ is —$OCH_2CH_2OCH_3$.

6. A method for controlling weeds, which comprises applying a herbicidally effective amount of (a) the herbicidal compound and a herbicidally effective amount of (b) amicarbazone, as defined in claim 1, to the weeds or to a place where they grow.

7. The method according to claim 6, wherein (a) the herbicidal compound is applied in an amount of from 1 to 1,000 g/ha and (b) amicarbazone is applied in an amount of from 1 to 3,000 g/ha.

8. The method according to claim 6, wherein (a) the herbicidal compound is at least one herbicidal compound selected from the group consisting of a benzoylpyrazole compound represented by the formula (I) and topramezone.

9. The method according to claim 6, wherein (a) the herbicidal compound is a benzoylpyrazole compound represented by the formula (I).

10. The method according to claim 9, wherein in the formula (I), each of $R^1$, $R^2$, $R^3$, $R^4$ and $R^6$ is methyl or ethyl, and $R^5$ is —$OCH_2CH_2OCH_3$.

11. The method according to claim 9, wherein in the formula (I), each of $R^1$ and $R^3$ is methyl or ethyl, each of $R^2$, $R^4$ and $R^6$ is methyl, and $R^5$ is —$OCH_2CH_2OCH_3$.

* * * * *